(12) United States Patent
Lech et al.

(10) Patent No.: US 9,058,816 B2
(45) Date of Patent: Jun. 16, 2015

(54) EMOTIONAL AND/OR PSYCHIATRIC STATE DETECTION

(75) Inventors: Margaret Lech, Melbourne (AU); Nicholas Brian Allen, Melbourne (AU); Ian Shaw Burnett, Melbourne (AU); Ling He, Melbourne (AU)

(73) Assignee: RMIT University, Melbourne (AU)

( * ) Notice: Subject to any disclaimer, the term of this patent is extended or adjusted under 35 U.S.C. 154(b) by 278 days.

(21) Appl. No.: 13/807,905

(22) PCT Filed: Aug. 23, 2010

(86) PCT No.: PCT/AU2010/001075
§ 371 (c)(1),
(2), (4) Date: Mar. 13, 2013

(87) PCT Pub. No.: WO2012/003523
PCT Pub. Date: Jan. 12, 2012

(65) Prior Publication Data
US 2013/0166291 A1      Jun. 27, 2013

(30) Foreign Application Priority Data
Jul. 6, 2010    (AU) .............................. 2010902987

(51) Int. Cl.
*G10L 25/48* (2013.01)
*G06F 17/27* (2006.01)
(Continued)

(52) U.S. Cl.
CPC ................. *G10L 17/26* (2013.01); *G10L 25/48* (2013.01); *G06F 19/3443* (2013.01)

(58) Field of Classification Search
CPC ......... G10L 17/26; G10L 25/48; G10L 13/04; G10L 25/00; G06F 19/3443; A61B 5/087; A61F 2002/206

USPC ......... 84/661, 663; 704/232, 261, 267, 270, 9
See application file for complete search history.

(56) References Cited

U.S. PATENT DOCUMENTS 5,528,726 A * 6/1996 Cook ............................ 704/261
5,911,170 A * 6/1999 Ding ............................. 84/661
(Continued)

OTHER PUBLICATIONS

France, Daniel Joseph; "Acoustical properties of speech as indicators of depression and suicidal Risk"; PHD Thesis; Vanderbilt University; ProQuest Dissertations & Theses (PQDT); Aug. 1997; 154pp.
(Continued)

*Primary Examiner* — Charlotte M Baker
(74) *Attorney, Agent, or Firm* — Christie, Parker & Hale, LLP

(57) ABSTRACT

Mental state of a person is classified in an automated manner by analysing natural speech of the person. A glottal waveform is extracted from a natural speech signal. Pre-determined parameters defining at least one diagnostic class of a class model are retrieved, the parameters determined from selected training glottal waveform features. The selected glottal waveform features are extracted from the signal. Current mental state of the person is classified by comparing extracted glottal waveform features with the parameters and class model. Feature extraction from a glottal waveform or other natural speech signal may involve determining spectral amplitudes of the signal, setting spectral amplitudes below a pre-defined threshold to zero and, for each of a plurality of sub bands, determining an area under the thresholded spectral amplitudes, and deriving signal feature parameters from the determined areas in accordance with a diagnostic class model.

18 Claims, 2 Drawing Sheets

(51) Int. Cl.
*G10L 17/26* (2013.01)
*G06F 19/00* (2011.01)

(56) References Cited

U.S. PATENT DOCUMENTS

| | | | |
|---|---|---|---|
| 6,480,826 B2 | 11/2002 | Pertrushin | |
| 7,283,962 B2 | 10/2007 | Meyerhoff et al. | |
| 7,451,079 B2 | 11/2008 | Oudeyer | |
| 7,571,101 B2 | 8/2009 | Humble | |
| 8,155,967 B2* | 4/2012 | Begel | 704/270 |
| 2008/0052080 A1 | 2/2008 | Narayanan | |

OTHER PUBLICATIONS

National Health and Medical Research Council; "Depression in Young People: Clinical Practice Guidelines"; Canberra: Australian Government Publishing Service; Mar. 1997; 195 pp.

Blumenthal Susan J., et al.; "Suicide Over the Life Cycle: Risk Factors, Assessment, and Treatment of Suicidal Patients"; Washington, D.C.; American Psychiatric Press; Chapter 6; Suicide and Psychiatric Diagnosis; 1990; 21pp.

Moore, Elliot, et al.; "Algorithm for automatic glottal waveform estimation without the reliance on precise glottal closure information" Proc. IEEE Int. Conf. Acoustic, Speech, Signal Processing; 2004; vol.1; pp. 101-104.

Moore II, Elliot, et al.; "Critical analysis of the impact of glottal features in the classification of clinical depression in speech," IEEE Transactions on Biomedical Engineering; vol. 55; No. 1; Jan. 2008; pp. 96-107.

Cohn, Jeffrey F., et al.; "Detecting Depression from Facial Actions and Vocal Prosody"; Proceedings Int. Conf. Affective Computing and Intelligent Interaction; 2009; 7pp.

France, Daniel Joseph, et al.; "Acoustical properties of speech as indicators of depression and suicidal risk"; IEEE Transactions on Biomedical Engineering; vol. 47; No. 7; Jul. 2000; pp. 829-837.

Ozdas, Asli; "Analysis of paralinguistic properties of speech for near-term suicidal risk assessment"; Ph.D. dissertation; Vanderbilt University; United States; Tennessee; 2001; 1pg.

Ozdas, Asli; et al.; "Investigation of vocal jitter and glottal flow spectrum as possible ones for depression and near-term suicidal risk"; IEEE Transactions on Biomedical Engineering; vol. 51; No. 9; Sep. 2004; pp. 1530-1540.

Low, Lu-Shih Alex, et al.; "Influence of Acoustic Low-Level Descriptors in the detection of clinical depression in adolescents"; IEEE; ICASSP 2010; pp. 5154-5157.

Low, Lu-Shih Alex, et al.; "Content based clinical depression detection in adolescents"; 17th European Signal Processing Conference (EUSIPCO 2009); Aug. 24-28, 2009; Glasgow, Scotland; 5pp.

Low, Lu-Shih Alex, et al.; "Mel Frequency Cepstral Feature and Gaussian Mixtures for Modeling Clinical Depression in Adolescents"; Proc. 8th IEEE Int. Conf. on Cognitive Informatics (ICCI'09); 2009; pp. 346-350.

He, Ling, et al.; "On the Importance of Glottal Flow Spectral Energy for the Recognition of Emotions in Speech"; Interspeech 2010; 2010 ISCA; Sep. 26-30, 2010; Makuhari, Chiba, Japan; pp. 2346-2349.

Torres, Juan, et al.; "Application of a GA/Bayesian Filter-Wrapper Feature Selection Method to Classification of Clinical Depression from Speech Data"; Soft Computing in Industrial Applications, ASC 39, pp. 115-121, 2007, Springer-Verlag Berlin Heidelberg; 8pp.

Moore II, Elliot, et al.; "Comparing objective feature statistics of speech for classifying clinical depression"; Proc. 26th Annual International Conference of IEEE EMBS, San Francisco, CA, USA, Sep. 1-5, 2004; pp. 17-20.

Moore II, Elliot, et al.; "Investigating the Role of Glottal Features in Classifying Clinical Depression"; Proc. 25th Annual International Conference of the IEEE EMBS; Cancun, Mexico; Sep. 17-21, 2003; pp. 2849-2852.

Goldberg Depression Questionnaire; http://counsellingresource.com/quizzes/goldberg-depression/index.html; accessed Jun. 29, 2010; 4pp.

Beck Depression Inventory; Wikipedia article; http://en.wikipedia.org/wiki/Beck_Depression_Inventory; accessed Jun. 29, 2010; 6pp.

International Preliminary Examination Report for corresponding International Application No. PCT/AU2010/001075, mailed Nov. 5, 2012, 7pp.

Written Opinion for corresponding International Application No. PCT/AU2010/001075 mailed Oct. 13, 2010, 7pp.

International Search Report for corresponding International Application No. PCT/AU2010/001075, mailed Oct. 13, 2010; 4pp.

\* cited by examiner

EMOTIONAL AND/OR PSYCHIATRIC STATE DETECTION

TECHNICAL FIELD

The present invention relates to a diagnostic method and device for assessing human mental, emotional and/or psychiatric health and state, based on speech analysis. In particular the present invention relates to automated methods applicable in real time for this purpose, utilising selected features of speech.

BACKGROUND OF THE INVENTION

Both stress and emotion are complex psycho-physiological states involving characteristic neurological and physiological responses. Stress is characterized by loss of ability to appropriately respond to difficult emotional and physical conditions. It is characterized by a subjective strain, dysfunctional physiological activity, and deterioration of performance. Existing stress detection and classification methods use stress categories bases on different levels of difficulties that a given person has to deal with (ex. low level stress, moderate stress, high level stress).

Emotion represents a complex psycho-physiological state characterised by a person's state of mind and the way an individual interacts with an environment. It is a relatively short-term state that lasts from minutes to hours, and it is characterised by type of emotion (ex. happy, angry, sad, anxious) as well as intensity of emotion.

Depression is a psychiatric state that belongs to the group of affective (or emotional) disorders in which emotional disturbances consist of prolonged periods (days to months) of excessive sadness. Emotionally, depression sufferers experience lasting feelings of hopelessness, anger, guilt, desperation and loneliness often leading to suicidal thoughts.

Depressive disorders seriously affect social, emotional, educational and vocational outcomes. It is also the most common precursor of suicide. It is estimated that up to one in eight individuals will require treatment for depressive illness in their lifetime.

The prevalence of depression, the world's fourth most serious health threat in 1990,is expected to rise steadily. About 10% of the Australian population experience depression severe enough to require medical attention. Early diagnosis is extremely useful and can mean a minimal disturbance of typical functioning and development of social and academic skills.

Currently the diagnosis of depression is based on observations of behavioural patterns, and interviews with parents and their family members. This process is time consuming and the illness is usually recognised only once in advanced stages. The current diagnosis is qualitative and largely based on the personal skills, experience and intuitive judgment of a mental health practitioner. The number of highly skilled professionals is limited, and their availability is generally restricted to major towns and health centres. As a result, each year, thousands of cases of depression are not being diagnosed and left untreated, leading to potential suicides.

Acoustical properties of speech have been experimentally investigated as indicators of depression and suicidal risk. These investigations have included prosodic, vocal tract and glottal speech features such as fundamental frequency (FO), amplitude modulation, formants, power spectral density, vocal jitter, glottal flow spectral slope and cepstral features.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect the present invention provides a method of classifying a current mental state of a person by analysing natural speech of the person, the method comprising:
  receiving a natural speech signal obtained from the person;
  extracting a glottal waveform from the speech signal;
  retrieving pre-determined parameters, the parameters being derived from selected training glottal waveform features, and the parameters defining at least one diagnostic class in accordance with a classifier;
  extracting the selected glottal waveform features from the glottal waveform of the speech signal; and
  classifying a current mental state of the person by comparing the extracted glottal waveform features with the parameters and classifier.

According to a second aspect the present invention provides a computing device for classifying a current mental state of a person by analysing natural speech of the person, the computing device comprising a processor configured to:
  receive a natural speech signal obtained from the person;
  extract a glottal waveform from the speech signal;
  retrieve pre-determined parameters, the parameters being derived from selected training glottal waveform features, and the parameters defining at least one diagnostic class in accordance with a classifier;
  extract the selected glottal waveform features from the glottal waveform of the speech signal; and
  classify a current mental state of the person by comparing the extracted glottal waveform features with the parameters and classifier.

According to a third aspect the present invention provides a computer program product comprising computer program code means to make a computer execute a procedure for classifying a current mental state of a person by analysing natural speech of the person, the computer program product comprising:
  computer program code means for receiving a natural speech signal obtained from the person;
  computer program code means for extracting a glottal waveform from the speech signal;
  computer program code means for retrieving pre-determined parameters, the parameters being derived from selected training glottal waveform features and the parameters defining at least one diagnostic class in accordance with a classifier;
  computer program code means for extracting the selected glottal waveform features from the glottal waveform of the speech signal; and
  computer program code means for classifying a current mental state of the person by comparing the extracted glottal waveform features with the parameters and classifier.

According to a fourth aspect the present invention provides a method of classifying a current mental state of a person by analysing natural speech of the person, the method comprising:

receiving a natural speech signal obtained from the person;
determining spectral amplitudes of the speech signal;
setting spectral amplitudes below a pre-defined threshold to zero, to produce thresholded spectral amplitudes;
for each of a plurality of sub bands, determining an area under the thresholded spectral amplitudes, and deriving signal feature parameters from the determined areas in accordance with a classifier;
retrieving pre-determined parameters, the parameters being derived from training signal features and the parameters defining at least one diagnostic class in accordance with the classifier; and
classifying a current mental state of the person by comparing the derived signal feature parameters with the pre-determined parameters and classifier.

According to a fifth aspect the present invention provides a computing device for classifying a current mental state of a person by analysing natural speech of the person, the computing device comprising a processor configured to:

receive a natural speech signal obtained from the person;
determine spectral amplitudes of the speech signal;
set spectral amplitudes below a pre-defined threshold to zero, to produce thresholded spectral amplitudes;
for each of a plurality of sub bands, determine an area under the thresholded spectral amplitudes, and derive signal feature parameters from the determined areas in accordance with a classifier;
retrieve pre-determined parameters, the parameters being derived from training signal features and the parameters defining at least one diagnostic class in accordance with the classifier; and
classify a current mental state of the person by comparing the derived signal feature parameters with the pre-determined parameters and classifier.

According to a sixth aspect the present invention provides a computer program product comprising computer program code means to make a computer execute a procedure for classifying a current mental state of a person by analysing natural speech of the person, the computer program product comprising computer program code means for receiving a natural speech signal obtained from the person;
computer program code means for determining spectral amplitudes of the speech signal;
computer program code means for setting spectral amplitudes below a pre-defined threshold to zero, to produce thresholded spectral amplitudes;
computer program code means for, for each of a plurality of sub bands, determining an area under the thresholded spectral amplitudes, deriving signal feature parameters from the determined areas in accordance with a classifier;
computer program code means for retrieving pre-determined parameters, the parameters being derived from training signal features and the parameters defining at least one diagnostic class in accordance with the classifier; and
computer program code means for classifying a current mental state of the person by comparing the derived signal feature parameters with the pre-determined parameters and classifier.

In embodiments of the second and fifth aspects of the invention, the computing device may comprise an electronic programmable device such as a DSP board, a mobile phone, a personal computer, a telephone, a personal communications device such as a PDA; a server effecting web-hosted processing; a point of care medical processor, or the like.

According to another aspect the present invention provides computer software for carrying out the method of either of the first or second aspects.

Some embodiments of the first to sixth aspects of the invention may further comprise selecting an optimal sub-set of the parameters, and utilising only the sub-set in subsequent classification.

The classifier may comprise a diagnostic class model, a trained neural network, or any other suitable classifier.

The current mental state of the person may comprise: current symptoms of depression of the person; current emotional state of the person; current stress level of the person; and/or current psychiatric state of the person.

The classifying of the current mental state of the person may involve classifying the person as being either: depressed; at-risk of developing depression; or non-depressed.

The method and device preferably outputs in near real-time a classification of the current mental state of the person. That is, in such embodiments a classification is produced substantially immediately upon utterance of the natural speech by the person.

In some embodiments of the first aspect, the glottal waveform feature extraction may be carried out in accordance with the method of the fourth aspect. Additionally or alternatively, the glottal waveform feature extraction in the first aspect may comprise deriving parameters from an area under normalised Teager Energy operator (TEO) correlation in one or more sub-bands, or may comprise other suitable glottal waveform feature extraction methods.

The pre-determined parameters may for example be retrieved from: onboard storage; or remote storage. The pre-determined parameters may have been previously determined by the same device which is performing the method of the present invention; or alternatively may have been previously determined elsewhere. For example it is expected that the pre-determined parameters may in some embodiments have been previously obtained by a suitable training process utilising natural speech signals obtained from a plurality of human subjects of known mental state. The parameters may be derived from the speech features by: stochastic modeling; statistical modeling; neural network modeling, or analytical modelling.

The method may further comprise pre-processing signal noise removal; channel compensation; pre-emphasis filtering; frame extraction; or other pre-processing. Wavelet Packet Analysis may be employed in parameter determination. These steps can improve the overall quality of speech and subsequently improve the classification results in situations when the speech samples are collected in noisy environments, over a communication channel which introduces channel noise and channel distortion and/or when the recording equipment is of low quality.

The method may be applied to independently classify stress, emotional state and state of depression. The mental state classified may be a psychiatric state such as depression.

The present invention is based on the recognition that the emotional state of a person suffering from a depressive disorder affects the acoustic qualities of his or her voiced speech, and that symptoms of depression might thus be detected through an analysis of the changes in the acoustical properties of speech. The present invention recognises that there is an important clinical and primary care need for a simple and reliable diagnostic test that can provide a rapid quantitative assessment of symptoms of clinical depression, and moreover risk for depression. This is particularly important in the diagnosis of the onset of depression which often occurs during childhood and adolescence. The present invention further recognises that there is also a need for a preventative assessment of risk for depression that may occur in the near future (for example within 1-5 years). In contrast to experimental techniques, the present invention recognises that such a clinical and primary care diagnostic must enable mass screening and should preferably produce highly accurate classification.

The present invention further recognises that classical models of speech production and speech prosody were produced largely for the purposes of telecommunication engineering. Unlike previous approaches to emotional speech analysis which assume that depression or emotional state influence speech parameters of such models, the present invention recognises that such classical models generally do not include mechanisms explicitly responsible for changes in speech acoustics due to stress, emotion or depression. The present invention instead exploits non-linear models of speech production to provide a closer link between emotional states, stress and depression and mechanisms of speech production. Parameters derived from these new models have been demonstrated to provide higher classification rates for stress, depression and some types of emotions when compared to the classical features derived from the linear models of speech production.

BRIEF DESCRIPTION OF THE DRAWINGS

An example of the invention will now be described with reference to the accompanying drawings, in which.

DESCRIPTION OF THE PREFERRED EMBODIMENTS

Figure 1:
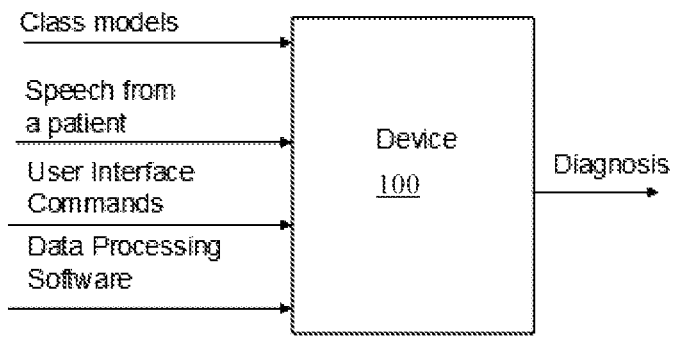
FIG. 1 is a schematic of a diagnostic device for classifying mental state and detection of depressive disorder and risk of depression in accordance with one embodiment of the invention, illustrating inputs and the output of the diagnostic device.

FIG. 1 is a schematic of a diagnostic device 100 for classifying mental state and detection of depressive disorder and risk of depression in accordance with one embodiment of the invention, illustrating inputs and the output of the diagnostic device 100. The device 100 reads the following inputs: data representing diagnostic class models data, signal processing software, speech samples from a patient being diagnosed, user interface commands data processing software. The device 100 produces as an output a medical diagnosis.

The device 100 in this embodiment has a programmable character. It can be implemented on a number of alternative hardware platforms such as: commercially available or custom built: computers, embedded computer systems, online www implementations, mobile phones, multimedia communication devices, local area networks terminals, stationary phones, digital signal processing boards, electronic microchips, nanotechnology communication devices and embedded and non-embedded medical communication devices.

The device 100 reads in the speech recordings from a patient being diagnosed, conducts analysis of these recordings and produces as an output a medical diagnosis.

Figure 2:
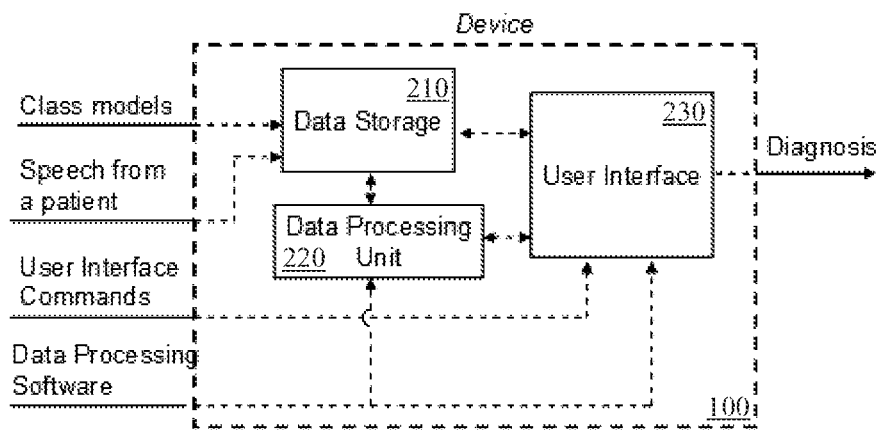
FIG. 2 is a functional block diagram of the device of FIG. 1.

FIG. 2 is a functional block diagram of the device of FIG. 1. The internal configuration of the device in this embodiment contains the following functional units: data storage 210, data processing unit 220 and user interface 230.

The device reads off-line a set of data representing models of diagnostic classes in a parametric form. The class models are generated off-line using a training procedure (discussed further in the following with reference to FIGS. 3-5). The diagnostic classes in this embodiment include: a non-depressed class, a number of classes representing various types of depression, and a number of classes representing different risks for developing depression in the near future.

The user interface 230 consists of software and hardware elements allowing the user to communicate with the device 100 by entering commands and receiving feedback response from the device 100. The data storage 210 stores the class models, operating software and patient's records including diagnosis and personal data. The data processing unit 220 executes the data processing software commands and the user interface commands.

The signal processing software includes signal processing schemes configured to receive and analyse a speech signal from the patient or person. The processing scheme consists of two stages: training and classification. FIG. 3 is a functional block diagram of a depression diagnosis method in accordance with one embodiment of the present invention, showing both a training stage 310 and a classification stage 360.

During the training stage 310 speech signals from individuals are pre-processed at 320. The individuals are already professionally diagnosed and classified as being either: depressed, non-depressed, or likely to become depressed within the next 1 to 5 years. Once the speech signals are pre-processed at 320 they are then used at 330 to calculate parameters called the characteristic features. The characteristic features are then used at 340 to generate models 350 of diagnostic classes in a parametric form.

The training process 310 can be performed either offline (at an earlier unrelated time) or online (at the time that diagnosis is required). When the training 310 is performed offline, the processing time can be relatively long and the resulting class models 350 can be stored and used in the testing stage 360 at the later time. When the training 350 is performed online, the processing time meets the requirements of the real-time processing for a given implementation platform.

The classification phase is applied to an individual for whom a diagnosis is desired, and for whom it is not known whether they are depressed, non-depressed or likely to develop depression within the next 1 to 5 years. During the classification phase 360, speech signal from the individual is pre-processed at 370 in the same or corresponding manner as occurs at 320 during training The pre-processed signal is then used at 380 to calculate characteristic features, using the same methodology as in the training process at 330. These characteristic features are then passed to the processing unit 220 which at 390 performs a pattern matching and a decision making task and provides a decision stating whether the tested signals represent an individual who is depressed, non-depressed or likely to develop depression in the next 1 to 5 years.

The pre-processing 320 and 370 in FIG. 3 refers to the process of speech enhancement which may include one or more of the following: removal of noise, communication channel compensation, pre-emphasis filtering and short-time frame extraction. The feature extraction 330 and 380 in FIG. 3 refers to the process of calculating parameters derived from speech analysis. Although different feature extraction methods can be used, the present embodiment of the invention uses two feature extraction methods selected for, and being recognised by the present invention as being particularly suited for, depression diagnosis and/or detection. These two feature extraction methods are referred to herein as: features type 1 and features type 2, discussed further in the following.

Figure 3A:
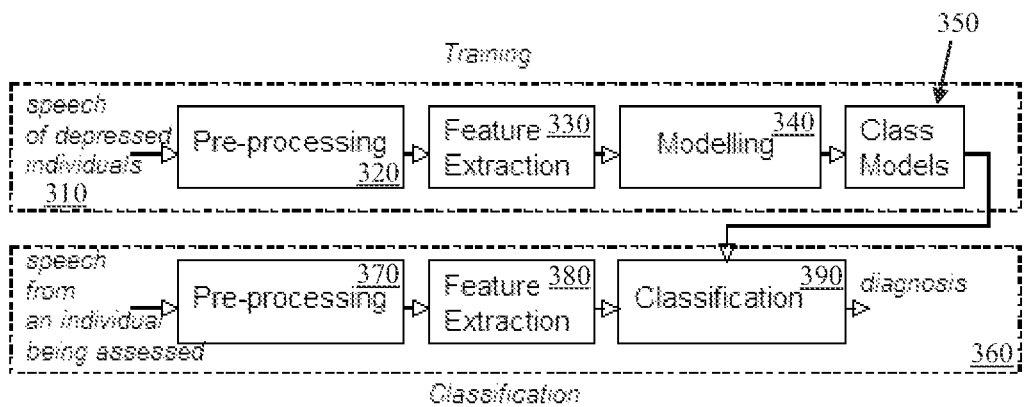
FIGS. 3a and 3b are functional block diagrams of depression diagnosis methods in accordance with two embodiments of the present invention, showing both a training stage and a classification stage.
Figure 3B:
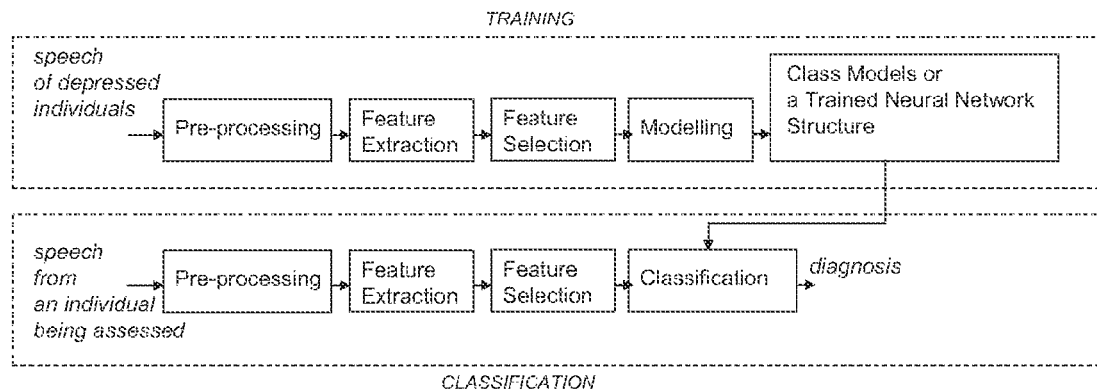

FIG. 3b illustrates an alternative embodiment to that shown in FIG. 3a. FIG. 3b corresponds to FIG. 3a, but with the addition of a feature selection step. Such a feature selection step is frequently used to reduce the number or volume of data by selecting an optimal sub-set of features, and discarding those that are redundant or of lesser use. FIG. 3b further comprises a Trained Neural Network Structure in addition to the Class Models, in recognition that the neural network approach can be interpreted not as a process of iterative training of models but as a process of generating weights values for a neural network structure to function as a classifier.

Figure 4:
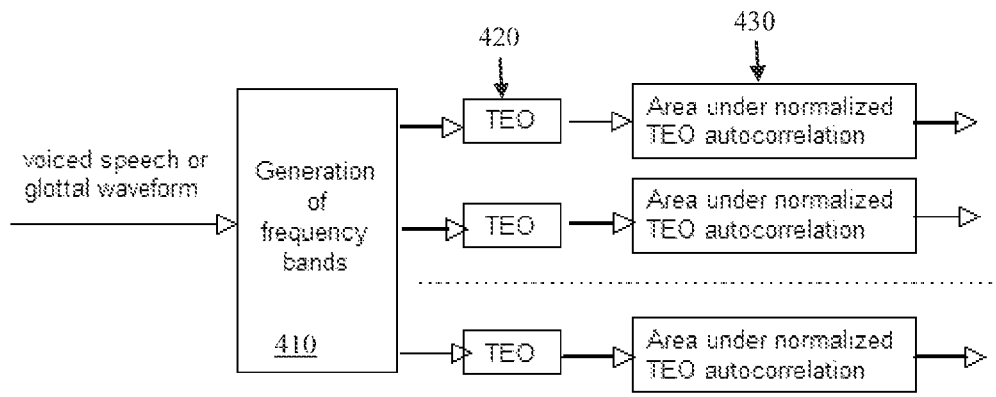
FIG. 4 illustrates calculation steps for extraction of features of type 1 in the embodiment of FIG. 3.

FIG. 4 illustrates calculation steps for extraction of features of type 1 in this embodiment. The speech or glottal waveform is divided into frequency bands at 410. The Teager Energy Operator (TEO) is calculated for each band at 420. The area under the normalized TEO autocorrelation of each band is calculated at 430 using Equation 1:

$$R_{\Psi(x)}[k] = \frac{1}{2M+1} \sum_{n=-M}^{M} \Psi(x[n])\Psi(x[n+k]) \quad (1)$$

Where x[n] represents a speech sample, M is the total number of samples in the analysed speech signal and $\Psi(x[n])$ is the Teager Energy Operator (TEO) given by Equation 2:

$$\Psi(x[n]) = x^2[n] - x[n+1]x[n-1] \quad (2)$$

The frequency bands can be calculated at 410 using the speech bandwidth subdivision in one of the following ways: subdivision into logarithmic bands, subdivision into octave bands or subdivision into linear bands.

Figure 5:
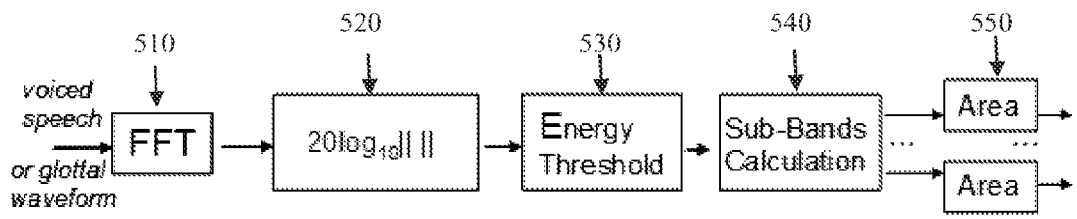
FIG. 5 illustrates calculation steps for extraction of features of type 2 in the embodiment of FIG. 3.

FIG. 5 illustrates calculation steps for extraction of features of type 2 in the embodiment of FIG. 3. The Fast Fourier Transform (FFT) algorithm is applied at 510 to the glottal waveform or to the voiced speech signal. The $20 \log_{10}$ of the amplitude spectrum is then calculated at 520. The log amplitude levels below an arbitrary constant threshold $\zeta$ are set to zero at 530. The value of $\zeta$ is predetermined.

The entire spectral range of the speech signal is then divided into frequency sub-bands at 540, and for each sub-band the area under the spectral envelope of log amplitudes is calculated at 550, generating vectors of feature parameters. The bandwidth sub-division at 540 can be performed using linear bands, logarithmic bands or octave bands.

The modelling in FIG. 3 refers to the process of building diagnostic class models using feature parameters derived from the speech signal.

The modelling technique can include stochastic models, statistical models, neural networks or analytical models. The modelling process can be supported by an optimization procedure and/or optimal feature selection procedure.

The classification in FIG. 3 refers to the process of making the final diagnosis decision. The decision making can be based either on the Bayesian decision theory or other procedure which maps a set of characteristic features into a set of the diagnostic classes.

This embodiment of the invention thus provides a method capable of quantitatively measuring specific motor changes in individuals susceptible to depression. This embodiment can be used to help physicians by taking some of the guesswork out of current diagnostic techniques. The automatic, computer-based analysis of speech conducted by this embodiment, indicating the probability of depression, may provide an important objective indicator that can be used as a mass-screening device, followed by more detailed (and more resource intensive) interview-based clinical diagnosis of depression. This embodiment may thus give an immediate quantitative assessment of the potential mental state of a patient, and thus help those in primary care roles, even if working in rural areas, to determine if a person showing certain emotional problems should seek professional help and further evaluation.

In other embodiments, the present invention may for example be used to provide an automatic speech analysis system for use in call centres or other telephony environments, to assess the level of depression and the suicide risk of callers and telephone users. The quantitative measure given by the diagnostic system in such embodiments will give physicians and therapists an improved metric by which they could gauge the effectiveness of various treatments in reducing depression and suicidality, such as cognitive, psychopharmacological, and electroconvulsive therapies used in depression.

An automatic speech analysis system could be used in call centres to assess the level of depression and the suicide risk of callers. Automatic speech analysis could be also be used to determine the emotional state of people working under high-risk and high-stress conditions that require an optimal state of mental health (e.g. heavy machinery operators, people working with dangerous chemicals, poisons and radioactive materials, construction workers, pilots).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of classifying a current mental state of a person by analysing natural speech of the person, the method comprising:
   receiving a natural speech signal obtained from the person;
   pre-processing the natural speech signal to effect frame extraction;
   extracting a glottal waveform from frames of the speech signal;
   retrieving pre-determined parameters, the parameters being derived from selected training glottal waveform features and the parameters defining at least one diagnostic class in accordance with a classifier;
   extracting selected glottal waveform features from the glottal waveform of the speech signal; and
   classifying the current mental state of the person by comparing the extracted selected glottal waveform features with the parameters and the classifier.

2. The method of claim 1, performed in near real-time upon utterance of the natural speech by the person.

3. The method of claim 1, wherein the classifying of the current mental state of the person involves classifying the person as being depressed; at-risk of developing depression; or non-depressed.

4. The method of claim 1, wherein extracting selected glottal waveform feature comprises deriving parameters from an area under a normalised Teager Energy operator (TEO) correlation in one or more sub-bands.

5. The method of claim 1 further comprising at least one further pre-processing step of: signal noise removal; channel compensation; and pre-emphasis filtering.

6. The method of claim 1 wherein Wavelet Packet Analysis is employed in derivation of the parameters.

7. The method of claim 1 wherein the parameters are derived from the selected training glottal waveform features by at least one of: stochastic modeling; statistical modeling; neural network modeling; and analytical modelling.

8. The method of claim 1, further comprising selecting an optimal sub-set of the parameters, and utilising only the optimal sub-set in subsequent classification.

9. The method of claim 1, wherein the classifier comprises a diagnostic class model.

10. The method of claim 1, wherein the classifier comprises a trained neural network.

11. A computing device for classifying a current mental state of a person by analysing natural speech of the person, the computing device comprising a processor configured to:
receive a natural speech signal obtained from the person;
pre-process the natural speech signal to effect frame extraction;
extract a glottal waveform from frames of the speech signal;
retrieve pre-determined parameters, the parameters being derived from selected training glottal waveform features and the parameters defining at least one diagnostic class in accordance with a classifier;
extract selected glottal waveform features from the glottal waveform of the speech signal; and
classify the current mental state of the person by comparing the extracted selected glottal waveform features with the parameters and the classifier.

12. The computing device of claim 11, wherein the computing device comprises at least one of: an electronic programmable device, a mobile phone, a personal computer, a telephone, a personal communications device; a server effecting web-hosted processing; and a point of care medical processor.

13. The computing device of claim 11, wherein the processor is further configured to perform the processes of claim 11 in near real-time upon utterance of the natural speech by the person.

14. A non-transitory computer storage medium comprising a plurality of computer program instructions to make a computer execute a process for classifying a current mental state of a person by analysing natural speech of the person, the process comprising:
receiving a natural speech signal obtained from the person;
pre-processing the natural speech signal to effect frame extraction;
extracting a glottal waveform from frames of the speech signal;
retrieving pre-determined parameters, the parameters being derived from selected training glottal waveform features and the parameters defining at least one diagnostic class in accordance with a classifier;
extracting selected glottal waveform features from the glottal waveform of the speech signal; and
classifying the current mental state of the person by comparing the extracted selected glottal waveform features with the parameters and the classifier.

15. A method of classifying a current mental state of a person by analysing natural speech of the person, the method comprising:
receiving a natural speech signal obtained from the person;
pre-processing the natural speech signal to effect frame extraction;
determining spectral amplitudes of frames of the speech signal;
setting the spectral amplitudes that are below a pre-defined threshold to zero, to produce thresholded spectral amplitudes;
for each of a plurality of sub bands, determining an area under the thresholded spectral amplitudes, and deriving signal feature parameters from the determined areas in accordance with a classifier;
retrieving pre-determined parameters, the parameters being derived from training signal features and the parameters defining at least one diagnostic class in accordance with the classifier; and
classifying the current mental state of the person by comparing derived signal feature parameters with the pre-determined parameters and the classifier.

16. A computing device for classifying a current mental state of a person by analysing natural speech of the person, the computing device comprising a processor configured to:
receive a natural speech signal obtained from the person;
pre-process the natural speech signal to effect frame extraction;
determine spectral amplitudes of frames of the speech signal;
set the spectral amplitudes that are below a pre-defined threshold to zero, to produce thresholded spectral amplitudes;
for each of a plurality of sub bands, determine an area under the thresholded spectral amplitudes, and derive signal feature parameters from the determined areas in accordance with a classifier;
retrieve pre-determined parameters, the parameters being derived from training signal features and the parameters defining at least one diagnostic class in accordance with the classifier; and
classify the current mental state of the person by comparing derived signal feature parameters with the pre-determined parameters and the classifier.

17. The device of claim 16, comprising at least one of: an electronic programmable device, a mobile phone, a personal computer, a telephone, a personal communications device; a server effecting web-hosted processing; and a point of care medical processor.

18. A non-transitory computer storage medium comprising a plurality of computer program instructions to make a computer execute a process for classifying a current mental state of a person by analysing natural speech of the person, the process comprising:
receiving a natural speech signal obtained from the person;
pre-processing the natural speech signal to effect frame extraction;
determining spectral amplitudes of frame of the speech signal;
setting the spectral amplitudes that are below a pre-defined threshold to zero, to produce thresholded spectral amplitudes;
for each of a plurality of sub bands, determining an area under the thresholded spectral amplitudes, and deriving signal feature parameters from the determined areas in accordance with a classifier;
retrieving pre-determined parameters, the parameters being derived from training signal features and the parameters defining at least one diagnostic class in accordance with the classifier; and classifying the current mental state of the person by comparing derived signal feature parameters with the predetermined parameters and the classifier.

* * * * *